United States Patent
Hoyte et al.

(10) Patent No.: US 10,555,747 B2
(45) Date of Patent: *Feb. 11, 2020

(54) POWER MORCELLATION IN A PROTECTED ENVIRONMENT

(71) Applicants: Lennox Hoyte, Tampa, FL (US); Anthony Imudia, Lutz, FL (US)

(72) Inventors: Lennox Hoyte, Tampa, FL (US); Anthony Imudia, Lutz, FL (US)

(73) Assignee: University of South Florida, Tampa, FL (US)

( * ) Notice: Subject to any disclaimer, the term of this patent is extended or adjusted under 35 U.S.C. 154(b) by 222 days.

This patent is subject to a terminal disclaimer.

(21) Appl. No.: 15/882,407

(22) Filed: Jan. 29, 2018

(65) Prior Publication Data

US 2018/0146973 A1 May 31, 2018

Related U.S. Application Data

(63) Continuation of application No. 14/689,713, filed on Apr. 17, 2015, now Pat. No. 9,877,739, which is a
(Continued)

(51) Int. Cl.
*A61B 17/32* (2006.01)
*A61B 17/00* (2006.01)
(Continued)

(52) U.S. Cl.
CPC .. *A61B 17/32002* (2013.01); *A61B 17/00234* (2013.01); *A61B 17/32* (2013.01);
(Continued)

(58) Field of Classification Search
CPC ...... A61B 2017/00287; A61B 17/0293; A61B 17/00234; A61B 17/32002;
(Continued)

(56) References Cited

U.S. PATENT DOCUMENTS 3,244,169 A 4/1966 Baxter
5,037,379 A 8/1991 Clayman
(Continued)

FOREIGN PATENT DOCUMENTS

WO 2013075103 A1 5/2013
WO 2013093030 A2 6/2013

OTHER PUBLICATIONS

Extended European Search Report for 15164942.3-1659 dated Jul. 15, 2015; Applicant: University of South Florida.

*Primary Examiner* — Katrina M Stransky
(74) *Attorney, Agent, or Firm* — Nicholas Pfeifer; Smith & Hopen, P.A.

(57) ABSTRACT

A power morcellation system, apparatus, and methodology. Structurally, the device includes a sturdy, pliable (e.g., able to be inserted and retracted through a 10-15 mm morcellator port), distensible, waterproof/watertight retaining bag/pouch/carrier to be deployed into the pelvic cavity of the subject. The device further includes a plurality (e.g., three (3)) of port tube channels extending outwardly from the bag, wherein the interior of each channel is in communication with the interior of the bag. Each channel has an open end (opposite from the end that terminates in the bag) through which a laparoscopic/robotic camera and other instruments (e.g., camera, control instrument) may pass. A smaller tube channel also extends outwardly from the bag and can be suited as an insufflation port channel, among other uses. The bag also includes a large opening surrounded by an elastic drawstring for receiving the specimen to be removed within the bag.

20 Claims, 11 Drawing Sheets

Related U.S. Application Data continuation of application No. 14/559,246, filed on Dec. 3, 2014, now Pat. No. 9,044,210.

(60) Provisional application No. 61/983,819, filed on Apr. 24, 2014, provisional application No. 62/019,097, filed on Jun. 30, 2014.

(51) Int. Cl.
  *A61B 17/34* (2006.01)
  *A61B 17/3205* (2006.01)
  *A61B 17/42* (2006.01)
  *A61B 90/40* (2016.01)

(52) U.S. Cl.
  CPC ...... *A61B 17/3205* (2013.01); *A61B 17/3431* (2013.01); *A61B 90/40* (2016.02); *A61B 2017/00287* (2013.01); *A61B 2017/00557* (2013.01); *A61B 2017/320024* (2013.01); *A61B 2017/320064* (2013.01); *A61B 2017/4216* (2013.01)

(58) Field of Classification Search
  CPC ..... A61B 2017/320024; A61B 17/221; A61M 13/003
  See application file for complete search history.

(56) References Cited

U.S. PATENT DOCUMENTS

| | | | |
|---|---|---|---|
| 5,074,867 A | 12/1991 | Wilk | |
| 5,279,539 A | 1/1994 | Bohan et al. | |
| 5,368,545 A | 11/1994 | Schaller et al. | |
| 5,465,731 A | 11/1995 | Bell et al. | |
| 5,480,404 A | 1/1996 | Kammerer et al. | |
| 5,522,790 A | 6/1996 | Moll et al. | |
| 5,562,603 A | 10/1996 | Moll et al. | |
| 5,611,803 A | 3/1997 | Heaven et al. | |
| 5,618,296 A | 4/1997 | Sorensen et al. | |
| 5,643,283 A | 7/1997 | Younker | |
| 5,653,705 A | 8/1997 | de la Torre et al. | |
| 5,769,794 A | 6/1998 | Conlan et al. | |
| 5,865,728 A | 2/1999 | Moll et al. | |
| 6,036,681 A | 3/2000 | Hooven | |
| 6,045,566 A | 4/2000 | Pagedas | |
| 6,206,886 B1 | 3/2001 | Bennardo | |
| 6,270,505 B1 | 8/2001 | Yoshida et al. | |
| 6,350,267 B1 | 2/2002 | Stefanchik | |
| 6,409,733 B1 | 6/2002 | Conlon et al. | |
| 6,685,628 B2 | 2/2004 | Vu | |
| 9,044,210 B1 * | 6/2015 | Hoyte | A61B 17/00234 |
| 9,877,739 B2 * | 1/2018 | Hoyte | A61B 17/00234 |
| 2003/0216611 A1 | 11/2003 | Vu | |
| 2004/0097960 A1 | 5/2004 | Terachi et al. | |
| 2004/0158261 A1 | 8/2004 | Vu | |
| 2007/0179458 A1 | 8/2007 | Leroy et al. | |
| 2008/0033451 A1 | 2/2008 | Reiber et al. | |
| 2008/0255519 A1 | 10/2008 | Piskun et al. | |
| 2009/0043315 A1 | 2/2009 | Moon | |
| 2010/0204548 A1 | 8/2010 | Bonadio et al. | |
| 2010/0318045 A1 | 12/2010 | Taylor et al. | |
| 2011/0011410 A1 | 1/2011 | Desai et al. | |
| 2011/0190780 A1 | 8/2011 | O'Prey et al. | |
| 2012/0016394 A1 | 1/2012 | Bonadio et al. | |
| 2013/0184536 A1 | 7/2013 | Shibley et al. | |
| 2013/0253267 A1 | 9/2013 | Collins | |
| 2013/0274758 A1 | 10/2013 | Young et al. | |
| 2014/0135788 A1 | 5/2014 | Collins | |
| 2014/0236167 A1 | 8/2014 | Shibley et al. | |
| 2014/0236168 A1 | 8/2014 | Shibley et al. | |

\* cited by examiner

POWER MORCELLATION IN A PROTECTED ENVIRONMENT

CROSS-REFERENCE TO RELATED APPLICATIONS

This nonprovisional application is a continuation of U.S. Nonprovisional application Ser. No. 14/689,713, entitled "Power Morcellation in a Protected Environment", filed Apr. 17, 2015, now U.S. Pat. No. 9,877,739, which is a continuation of U.S. Nonprovisional application Ser. No. 14/559,246, entitled "Power Morcellation in a Protected Environment", filed Dec. 3, 2014, now U.S. Pat. No. 9,044,210, which claims priority to U.S. Provisional Application No. 61/983,819, entitled "Power Morcellation in a Protected Environment", filed Apr. 24, 2014, and to U.S. Provisional Application No. 62/019,097, entitled "Power Morcellation in a Protected Environment", filed Jun. 30, 2014, all of which are incorporated herein by reference in their entireties.

BACKGROUND OF THE INVENTION

1. Field of the Invention

This invention relates, generally, to morcellators. More specifically, it relates to power morcellation in a protected environment in order to eliminate the risk of tumor spread.

2. Brief Description of the Prior Art

Since the introduction of minimally invasive gynecologic surgeries in the late 1990s, millions of patients have benefited enormously from this technological advancement. Minimally invasive hysterectomy and myomectomy through either traditional laparoscopy or robotic assistance has been possible due to the use of open mechanical power morcellation as a means of retrieving the surgical specimen.

While this open mechanical power morcellation has been advantageous in facilitating these complex surgeries, it has the disadvantage of potentially spreading previously undiagnosed uterine malignancy during the process. See R. Barbieri, Benefits and pitfalls of open power morcellation of uterine fibroids, OBG Manag. 2014;26(2):10-15, which is incorporated herein by reference. Recently, the Food & Drug Administration ("FDA") issued a safety communication discouraging the use of open laparoscopic power morcellation for the surgical removal of the uterus following hysterectomy or uterine fibroids following myomectomy in women. This safety communication was issued because this type of procedure poses the risk of disseminating unsuspected malignant tissue, such as uterine sarcomas. To continue to harness the multiple benefits of minimally invasive gynecologic surgeries, it is imperative that laparoscopic surgeons devise a safe alternative to current open power morcellation.

Attempts have been made to overcome the drawbacks of open mechanical power morcellation. For example, U.S. patent application Ser. No. 13/725,148 to Shibley et al. discusses a pneumoperitoneum device having a tissue bag that is inserted through a laparoscopic port of a subject. Generally, a tissue bag with an opening into its interior and ring element defining the opening is inserted into the body through the laparoscopic port. The bag is manipulated to place an excised tissue (e.g., uterus) inside the bag. The ring element is then pulled outside the body through the laparoscopic port. At this point, a number of laparoscopic tools can be inserted into the bag through the port to insufflate and morcellate the excised tissue therewithin. Shibley et al. also contemplates a trocar (though another laparoscopic port) piercing the bag after insufflation for insertion of other tools. When the tissue is morcellated or otherwise ready for removal, the bag enclosing the tissue is pulled out of the original laparoscopic port to remove the tissue. However, there are several drawbacks to this methodology. It takes additional time to fold and pull the ring element into and out of the laparoscopic port. There is also the potential for unnecessary complications (i.e., similar to those found in previous open morcellation procedures) by not sealing the bag within the body and pulling the open top out through the port. Insufflating after pulling the ring out of port also limits the number of ports and tools that can access the interior of the bag, as there are risks of compromising the insufflation when piercing the insufflated bag.

Accordingly, what is needed is a power morcellation system that eliminates the risk of inadvertent tissue dissemination via morcellation in a protected environment and does not disrupt the existing endoscopic workflow. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY OF THE INVENTION

The long-standing but heretofore unfulfilled need for an improved, more effective and lower cost shape-shifting surface is now met by a new, useful, and nonobvious invention.

In an embodiment, the current invention is a morcellation system. The system includes a flexible retaining bag, pouch, or carrier with a specimen-receiving opening that leads from an exterior of the retaining bag to a substantially hollow interior of the retaining bag. The bag is insertable into an abdominal or pelvic cavity of a subject or patient. The bag is structured to receive a targeted, excised specimen within the interior of the bag. The system further includes a means of tightening, cinching, closing, or sealing the specimen-receiving opening positioned on the perimeter of the opening. A plurality of elongate, flexible laparoscopic tool- or trocar-receiving channels extend externally from a lining of the retaining bag at a spaced distance away from the specimen-receiving opening and at a spaced distance away from each other. The channels are positioned on the lining of the bag, such that the channels line up with the laparoscopic ports on a body of the subject. The channels further are structured to receive one or more laparoscopic tools. Each channel has a proximal end and a distal end, where the distal end terminates at the body of the retaining bag within the operative internal cavity of the subject and the proximal end is external to the body of the subject. Each channel also has a substantially hollow interior that is in communication with the hollow interior of the retaining bag. The retaining bag has a first position and a second position. The first position is the bag in a desufflated position within the operative internal cavity of the subject with the specimen-receiving opening being open. The second position is the bag in an insufflated position within the abdominal or pelvic cavity of the subject with the specimen-receiving opening being closed.

The operative internal cavity of the subject may be an abdominal or pelvic cavity.

The laparoscopic tool(s) inserted into the channels may be a trocar, morcellator, a camera, a control instrument, or an insufflation source.

The specimen-receiving opening can be tightened, cinched, closed, or sealed using a drawstring-type apparatus that is pulled relative to the opening in order to reduce a diameter or length of the opening. Alternatively, the specimen-receiving opening can be retrieved through one of the ports and tightened against the trocar to maintain pneumoperitoneum.

The channels may include a morcellator channel receiving a morcellator, a camera channel receiving a channel, and a control instrument channel receiving a control instrument, such that the morcellator could morcellate the specimen within the interior of the bag. In this case, the morcellator can morcellator the targeted specimen within the retaining bag under direct visualization of the camera while the control instrument holds the specimen.

The channels may each include an elongate suture tag attached to and positioned at the second end in order to facilitate laparoscopic manipulation of the channel.

In the second insufflated position, the insufflated bag may be pressed up against the anterior abdominal wall within the subject.

In a separate embodiment, the current invention is a method of performing minimally invasive laparoscopic surgery on a subject. Laparoscopic ports are provided in the body of the subject, and the targeted specimen is excised within the operative internal cavity of the subject. The morcellation system is inserted into the abdominal or pelvic cavity of the subject in a deflated position. The morcellation system includes a retaining bag having a substantially hollow interior and having a sealable or closeable specimen-receiving opening, where the specimen-receiving opening provides for completely open communication between the operative internal cavity of the subject and the interior of the retaining bag. The morcellation system further includes a plurality of laparoscopic tool- or trocar-receiving channels extending from the lining of the bag. The channels have a hollow interior that is in open communication with the interior of the bag. The channels each have a first end that terminates at the body of the bag within the abdominal or pelvic cavity of the subject, and a second end that is external to the body of the subject when the system is inserted into the subject. The channels are spatially aligned with the laparoscopic ports on the body of the subject and are positioned at a spaced distance away from the specimen-receiving opening and at a spaced distance from each other.

Each channel is withdrawn from the operative internal cavity through its corresponding, spatially aligned laparoscopic port. The excised specimen is positioned/placed into the interior of the retaining carrier through the specimen-receiving opening. The opening is tightened, cinched, closed, or sealed in order to enclose the specimen within the carrier. The interior of the carrier is no longer in completely open communication with the operative cavity of the subject. Laparoscopic tool(s) are inserted into each channel, so that the distal end of each laparoscopic tool is positioned within the interior of the carrier and the proximal end of each laparoscopic tool is disposed external to the subject's body. The carrier is then insufflated to distend in order to form a protected environment. The enclosed specimen can then be morcellated within the insufflated carrier to remove the specimen from the operative cavity of the subject. Once completed as much as desired, the retaining carrier can be desufflated and the morcellation system withdrawn/removed from the subject's body through a laparoscopic port. The retaining carrier would enclose any remnants of the specimen.

The operative internal cavity of the subject may be an abdominal or pelvic cavity.

The laparoscopic tool(s) inserted into the channels may be a trocar, morcellator, a camera, a control instrument, or an insufflation source.

The specimen-receiving opening can be tightened, cinched, closed, or sealed using a drawstring-type apparatus that is pulled relative to the opening in order to reduce a diameter or length of the opening.

The channels may include a morcellator channel receiving a morcellator, a camera channel receiving a channel, and a control instrument channel receiving a control instrument, such that the morcellator could morcellate the specimen within the interior of the bag. In this case, the morcellator can morcellator the targeted specimen within the retaining bag under direct visualization of the camera while the control instrument holds the specimen.

The channels may each include an elongate suture tag attached to and positioned at the second end in order to facilitate laparoscopic manipulation of the channel.

The excised, targeted specimen being morcellated may be a uterus in a female subject.

In the second insufflated position, the insufflated bag may be pressed up against the anterior abdominal wall within the subject.

The step of withdrawing each channel from the operative cavity can be performed as follows. A grasper can be inserted into a first laparoscopic port and withdrawing a first channel. This can be repeated for withdrawing a second channel from a second laparoscopic port. In this case, the step of tightening the specimen-receiving opening is performed after withdrawing the first channel but before withdrawing the second channel.

The step of withdrawing or removing the morcellation system from the operative cavity can be performed as follows. Each channel, except for one (1), can be inserted back into the operative cavity after the laparoscopic tools have been removed. The remaining channel can then be pulled in order to extract the retaining carrier and each channel from the operative cavity.

Each of the foregoing steps may be performed under direct visualization of a camera.

In a separate embodiment, the current invention may be any structure or method for performing a surgical procedure in a protected environment within an operative internal cavity of a subject or patient. The structure or method can have any one or more of the foregoing limitations.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIG. 2A is a cross-sectional view of a subject's body with a user-operated grasper grasping a channel within the cavity. FIG. 2B is a cross-sectional view of the subject's body with the channel of FIG. 2A pulled/withdrawn through a laparoscopic port via the user-operated grasper. FIG. 2C is a cross-sectional view of the subject's body with four channels each pulled/withdrawn through a respective laparoscopic port. FIG. 2D is a top view of the subject's body with four channels each pulled/withdrawn through a respective laparoscopic port.

FIG. 5A depict channels extending out of the subject's body with laparoscopic tools (other than the camera) removed. FIG. 5B depicts removal of the camera and two of the channels being inserted back into the abdominal/pelvic cavity of the subject. FIG. 5C depicts three of the channels inserted into the abdominal/pelvic cavity of the subject with the morcellator channel still extending out of the subject's body. FIG. 5D depicts removal of the morcellation system from the subject's body through the morcellation port.

DETAILED DESCRIPTION OF THE PREFERRED EMBODIMENT

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

Figure 1:
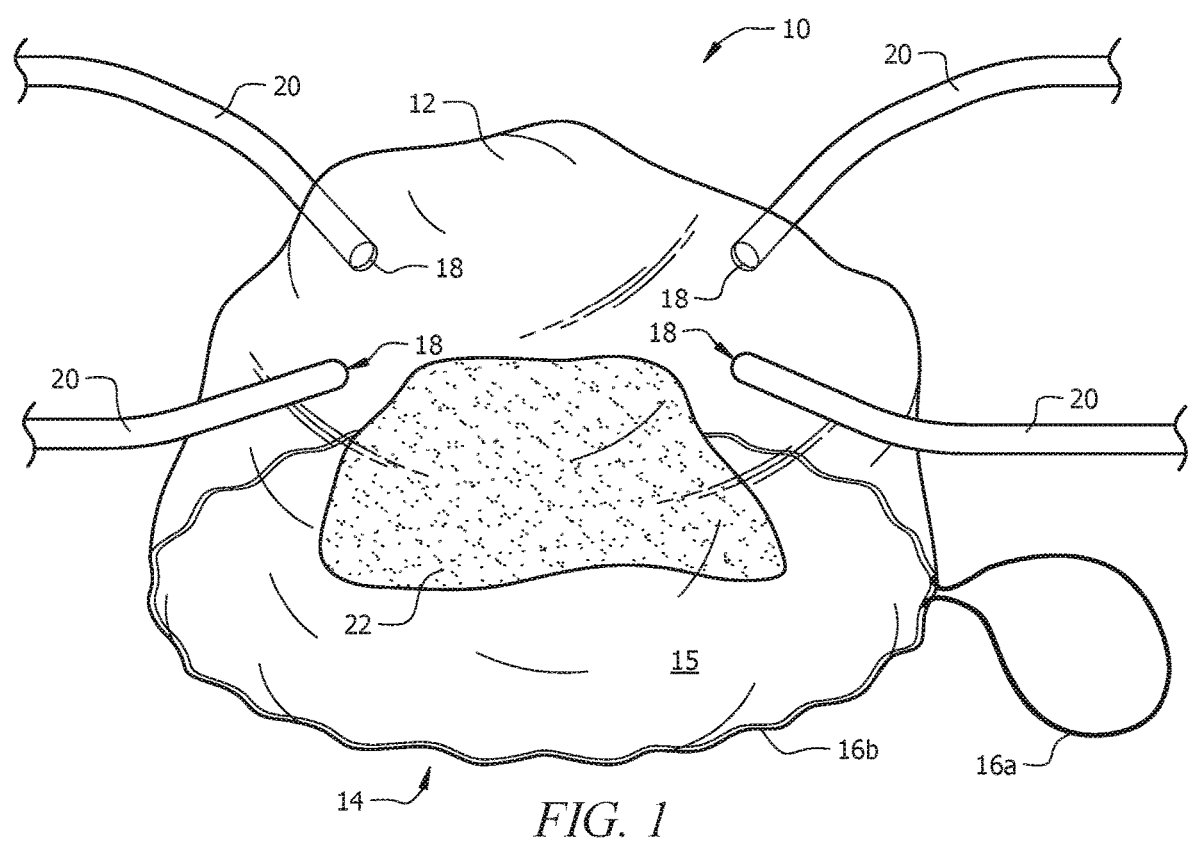
FIG. 1 depicts a structure of a power morcellation system according to an embodiment of the current invention.

In an embodiment, as seen in FIG. 1, the current invention is a power morcellation system, generally denoted by the reference numeral 10, that includes a sturdy, pliable (e.g., able to be inserted and retracted through a ~10-15 mm morcellator port), distensible, waterproof/watertight/water-resistant retaining bag/pouch/carrier, denoted by the reference numeral 12, to be deployed into an operative or targeted (e.g., pelvic, abdominal, peritoneal) cavity of a subject or patient. Carrier 12 also includes large base opening 14 surrounded by elastic drawstring 16a, 16b for receiving specimen 22 to be removed within carrier 12.

Carrier 12 has a plurality of apertures 18 positioned at a spaced distance away from opening 14. Aligned with and extending from apertures 18 is a plurality (e.g., at least three (3) or four (4)) of port tube channels 20 extending outwardly from carrier 12, wherein the interior of each channel 20 is in communication with interior 15 of carrier 12. Each channel 20 has an open proximal end (opposite from the distal end that terminates in apertures 18 of carrier 12) through which a laparoscopic/robotic camera and other instruments (e.g., camera, control instruments, morcellator, etc.) may pass.

Methodologically, upon properly creating laparoscopic ports leading to the targeted cavity of the subject according to conventional methods, carrier 12 of morcellation system 10 is brought into the endoscopic field after specimen 22 to be removed is separated from the surrounding tissue. Specimen 22 is placed into carrier 12 via large opening 14 of carrier 12, and drawstring 16a is pulled to tighten surrounding drawstring 16b so that large opening 14 is cinched or closed. Drawstring 16a can optionally be retrieved using an endoscopic Carter-Thompson type retriever needle, passed transabdominally. The neck of the cinched large opening can be held against the anterior abdominal wall, so as to restrict the escape of fluid from the cinched large opening.

Port channels 20 are individually pulled back through the laparoscopic ports (e.g., camera port, morcellator port, control instrument port) that lead to the targeted or operative cavity.

As will become clearer as this specification continues, a smaller tube channel can also extend outwardly from carrier 12 and can be suited as an insufflation port channel, among other uses. The smaller port channel can be brought out through a smaller (e.g., 3 mm) trocar port and can be used to insufflate carrier 12. The camera, standard morcellator, and control instruments can then be maintained in or reinserted into carrier 12, which is inside the operative (e.g., abdominal) cavity. Carrier 12 is insufflated via the insufflation channel, such that it distends to line the peritoneal cavity. Carrier 12 may be able to withstand insufflation pressures of ~20-40 hhMg.

The morcellation is conducted in a typical manner, under direct visualization, with the distal end of the camera and control instrument positioned within interior 15 of insufflated carrier 12, along with the standard morcellator and extraction instrument. If extraneous tissue pieces of specimen 22 break free during the morcellation, these are automatically retained within interior 15 of carrier 12.

When the larger pieces of targeted specimen 22 are removed via the morcellator, carrier 12 can be suctioned to retrieve the smaller remnants, and the instruments can be removed from ports 20. Port channels 20 can then be tied off, and carrier 12 (which would now be substantially empty) can be withdrawn sealed and intact via one of ports 20, for example the larger morcellator port. Laparoscopic port extraction and closure can be performed in a standard fashion.

In an embodiment, the current invention keeps all tissue pieces inside a sealed cavity, eliminating the risk of tissue dispersal into the peritoneal cavity. Morcellation can be accomplished under direct visualization, while the targeted tissue is sealed within the retaining bag or carrier. Normal, healthy, or non-targeted tissue can then be kept or maintained outside of the field of morcellation. The current methodology is user-friendly for deployment and extraction of the device and contents, and standard laparoscopic/robotic equipment can be used. The invention requires only deployment of the carrier and thus fits into the existing laparoscopic workflow at a minimal manufacturing cost.

EXAMPLE

FIGS. 2A-6 depict an exemplary structure and methodology of the power morcellation system, apparatus, and method, according to an embodiment of the current invention. The morcellation system is generally denoted by the reference numeral 10.
Structure Structurally, as also seen in FIG. 1, power morcellation system 10 includes flexible retaining bag, pouch, or carrier 12 with large, typically circular specimen-receiving opening or aperture 14 that has a diameter/length and leads from the exterior of carrier 12 to substantially hollow interior 15 of carrier 12.

The perimeter of specimen-receiving opening 14 can be lined with means of tightening, cinching or closing 16b carrier 12 or opening 14 by bringing all sides of the perimeter of opening 14 closer to one another, thus reducing or completely eliminating the diameter/length of specimen-receiving opening 14 as means of tightening, cinching, or closing 16a, 16b is actuated. Examples of means of tightening, cinching, or closing 16a, 16b include, but are not limited to, a drawstring-type apparatus that can be pulled relative to opening 14 to tighten or close opening 14, a monofilament suture that can be tied to cinch opening 14, a locking cable/zip tie-type apparatus that can be pulled relative to opening 14 to seal opening 14, and other known apparatuses and methods of tightening, cinching, or closing specimen-receiving opening 14. Through any of these means, specimen-receiving opening 14 can be tightened, cinched, or closed to hinder or prevent insufflating medium (gas) or any tissue inside carrier 12 from exiting interior 15 of carrier 12 through the specimen-receiving opening 14.

A plurality of flexible laparoscopic tool- or trocar-receiving channels, generally denoted by the reference numeral 20, extends externally from carrier 12 at a spaced distance away from specimen-receiving opening 14. Channels 20 have a proximal end that is closest to user 30 and may be free (i.e., not attached to anything at least initially), and also a distal end that terminates at carrier 12. Channels 20 have a substantially hollow interior that is in open communication with interior 15 of carrier 12.

Typically, at least three (3) to four (4) channels are needed—1 for the morcellator, 1 for the control instrument, 1 for the camera, and 1 for insufflation. However, any number of port channels 20 are contemplated by the current invention. For example, one of the channels, such as the channel used for the camera, can also be utilized to link the insufflation source to substantially hollow interior 15 of carrier 12. Alternatively, another separate channel can be used for the insufflation source. Alternatively, even just one (1) laparoscopic port can be sufficient for the system 10, in particular if a camera is released or implanted within operative cavity 23 of the subject (see U.S. Pat. No. 8,416,342) and/or if a female subject's vagina is used as a laparoscopic port for the morcellator (see PCT App. No. PCT/US2013/050085) and/or if the control instrument and insufflation source use the same laparoscopic port using an integrated trocar, for example. One (1) laparoscopic port may even be suitable if using single-port laparoscopic techniques.

In an embodiment, conventional trocars (not shown) can be placed inside each channel 20. This can have the advantage of insufflating normally via an already-existing channel, such as the camera trocar insufflation point. An additional advantage of having a trocar inside each channel 20 is that it can facilitate manipulation of laparoscopic instrumentation without running the risk of perforating or otherwise damaging flexible channels 20.

Laparoscopic tool- or trocar-receiving channels 20 are positioned on and extend from carrier 12 so that channels 20 line up with the normal laparoscopic port placement (see reference numeral 26) on body 24 of the subject, with appropriate tolerances to allow for variations in placement of laparoscopic ports 26. Channels 20 are positioned at a spaced distance away from specimen-receiving opening 14 and at a spaced distance away from each other. Channels 26 typically are elongate and are structured to snugly fit various laparoscopic tools that can extend into interior 15 of carrier 12 via channels 26.

Each channel 20 may further include a long suture tag (not shown) at its open proximal end (opposite from its distal end terminating at retaining carrier 12) to facilitate laparoscopic manipulation, such as pulling the channel through the appropriate laparoscopic port 26.

When specimen-receiving opening 14 is tightened, cinched, or sealed via means 16a, 16b, excised tissue or specimen 22 can be sealed or otherwise contained within substantially interior 15 of carrier 12. Cinched opening 14 can be held to the anterior wall of the operative or targeted (e.g., abdominal, pelvic, peritoneal) cavity through the morcellator port and channel (or other existing laparoscopic port and channel) using a conventional laparoscopic tenaculum (not shown).

Power morcellation system/apparatus 10, in particular specimen-receiving carrier 12 and laparoscopic tool- or trocar-receiving channels 20 extending therefrom, is typically formed of pliable materials, such as flexible plastics, to permit entry and exit from one or more of laparoscopic ports 26 (e.g., removing carrier 12 and channels 20 through the morcellator port).
Methodology The following steps are described in a manner and order that is not intended to be limiting of the scope of the current invention. It is contemplated herein that the order of the steps described herein can be altered or rearranged so long as the ultimate results of the steps remain the same or similar. This will become clearer as this specification continues.

Laparoscopic ports 26, typically at least three (3) or four (4) or more, are created in body 24 of the subject/patient according to conventional methods for surgical positioning of laparoscopic tools 20. If three (3) ports 24 are formed, ports 24 can function as a morcellator port (10-15 mm), a camera port, and a control instrument port. One of these ports can be used as the insufflation port as well, or a fourth port can be created for insufflation. Any number of laparoscopic ports 24 are contemplated by the current invention. For example, even just one (1) laparoscopic port can be sufficient for the system 10, in particular if a camera is released or implanted within operative cavity 23 of the subject (see U.S. Pat. No. 8,416,342) and/or if a female subject's vagina is used as a laparoscopic port for the morcellator (see PCT App. No. PCT/US2013/050085) and/or if the control instrument and insufflation source use the same laparoscopic port using an integrated trocar, for example. One (1) laparoscopic port may even be suitable if using single-port laparoscopic techniques.

Targeted tissue 22 (e.g., uterus, fibroid, etc.) is excised within interior or operative cavity 23 of body 24 using known endoscopic methods. Upon excising targeted tissue 22 using known methods (e.g., via the planned or intended morcellator port), the trocar is removed from the port (e.g., the planned or intended morcellator port), and the port skin incision can be enlarged as needed. At this point, laparoscopic ports 26 have been formed leading from the external environment to interior 23 (e.g., abdominal or pelvic cavity) of body 24, and targeted tissue 22 is contained within interior 23 (e.g., abdominal or pelvic cavity) of body 24.

Next, power morcellation system/apparatus 10 can be inserted into interior 23 of body 24 of the patient or subject via one of ports 26, typically the largest port, which may be the morcellator port. Flexible/Foldable retaining bag, pouch, or carrier 12 and laparoscopic tool- or trocar-receiving channels 20 extending from carrier 12 are passed through one of laparoscopic ports 26 into operative/peritoneal cavity 23, typically under camera visualization.

In addition to the drawstring-type apparatus or other means of tightening, cinching, or closing 16a, 16b retaining carrier 12 or specimen-receiving opening 14, each channel 20 can include a long suture tag (not shown) on its open proximal end (opposite from the distal end of channel 20 terminating in retaining carrier 12) to facilitate laparoscopic manipulation and manipulation of channels 20. Accordingly, the entirety of power morcellation system 10 is inserted into interior 23 of body 24 of the subject, primarily including retaining carrier 12 and channels 20. This can be seen in FIG. 2A.

Still referring to FIG. 2A, grasper 28 can subsequently be inserted through one of ports 26 (e.g., the morcellator port or skin incision) by user 30. Grasper 28 can used to withdraw one of channels 20 through one of ports 26, typically morcellator channel 30c (see FIGS. 3A-3B) through laparoscopic port 26 that was created for morcellator 32. Morcellator 32 itself can then be passed into retaining carrier 12 through morcellator channel 20c. If needed, morcellator channel 20c can be sealed around the morcellator trocar with a suture tie (not shown). Alternatively, control instrument channel 20a, camera channel 20b, or insufflation channel 20d can be withdrawn through their respective laparoscopic ports 26, rather than withdrawal of morcellator port 20c.

At this point or at a later time (or even prior to this point), excised tissue or specimen 22 can then be placed into interior 15 of retaining carrier 12 through specimen-receiving opening 14 under camera visualization using graspers (such as grasper 28) inserted into operative cavity 23 via operating trocar ports 26. At this point, morcellator channel 20c has been pulled through its respective morcellator port 26, such that the free/proximal end of channel 20c is external to body 24 of the subject, and specimen 22 is positioned within interior 15 of carrier 12.

Figure 3A:
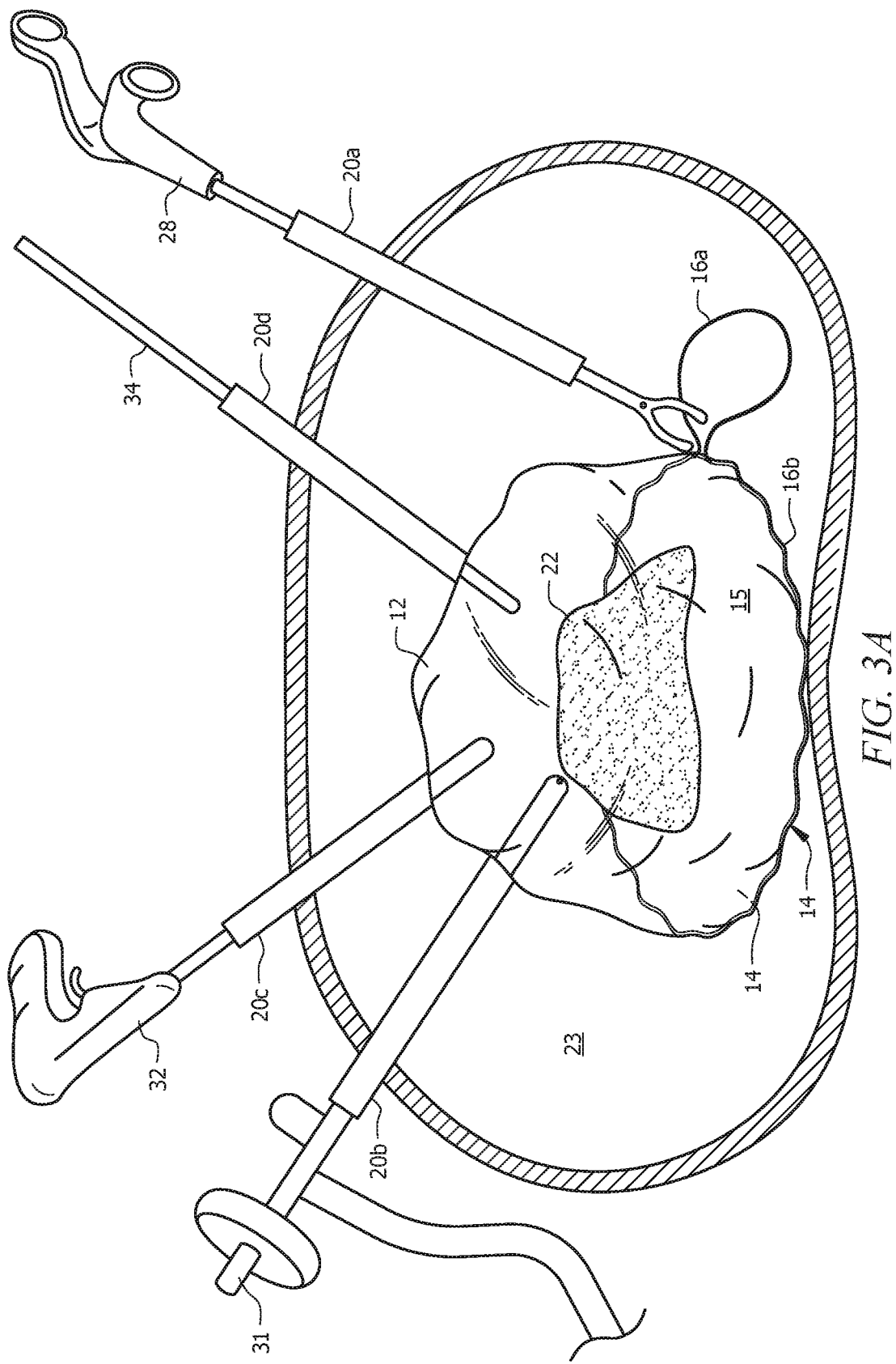
FIG. 3A is a cross-sectional view of a portion of a user's pelvic cavity with an open retaining bag/carrier contained therein and with laparoscopic tools inserted into the channels of the system and into the interior of the retaining bag. A grasper can also be seen attempting to grasp a drawstring for tightening or closing the opening that receives the specimen to be removed.
Figure 3B:
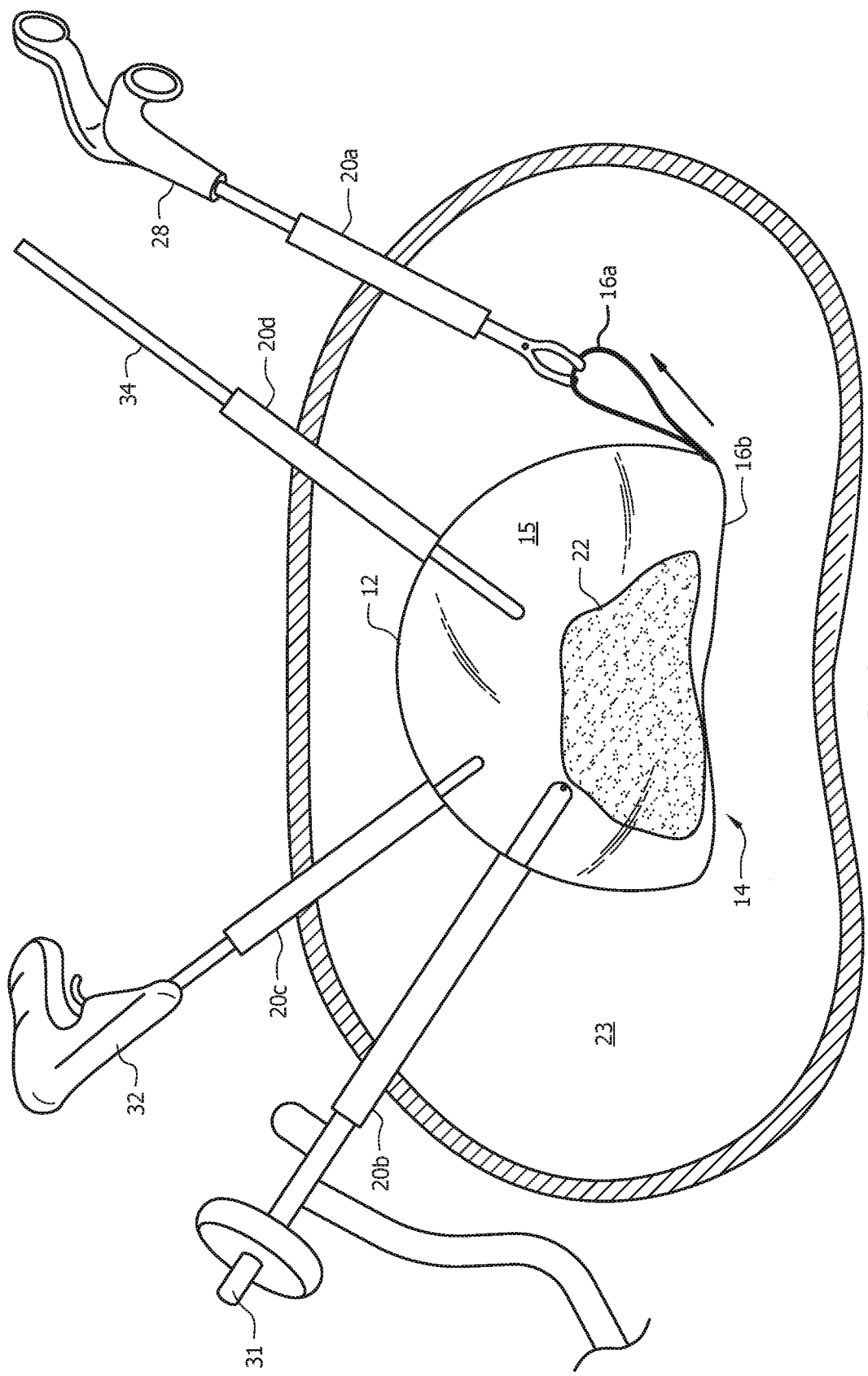
FIG. 3B depicts the positioning of FIG. 3A except with the grasper tightening the drawstring in order to tighten or close the opening that receives the specimen to be removed. As such, the specimen can be sealed within the interior of the retaining bag.

At this point or at a later time (or even prior to this point if specimen 22 has been placed into interior 15 of carrier 12), opening 14 of carrier 12 can be cinched, closed, or sealed via means 16a, 16b. If a drawstring-type apparatus is used as means of closing 16a, 16b specimen-receiving opening 14, as seen in FIGS. 3A-3B, a suture retrieval needle (e.g., CARTER-THOMASON type) or other grasper (such as grasper 28 seen) can be passed transcutaneously through one of laparoscopic ports 26 to retrieve and/or pull the ends of the drawstring-type apparatus or other means 16a, 16b. This can be done to cinch opening 14, for example against the anterior abdominal wall, to form a relatively airtight seal and secure/clamp drawstring-type apparatus 16a in place within operative cavity 23. This can be seen in FIGS. 3A-3B, where FIG. 3A shows opening 14 in an open position and FIG. 3B shows opening 14 in a closed or cinched position. Alternatively, a knot can be tied in drawstring 16a, and opening 14 can be cinched with a knot pusher intracorporeally to ensure airtightness.

Alternatively, the specimen-receiving opening can be retrieved through one of the ports and tightened against the trocar to maintain pneumoperitoneum.

Though not required, the benefit of withdrawing channel 20c prior to actuating means 16a, 16b is for stability of system 10 during actuation of means 16a, 16b. For example, if means 16a, 16b is the drawstring shown in the figures, then channel 20c can be held outside of body 24 of the subject while drawstring 16a is pulled to tighten surrounding drawstring 16b. However, depending on which means 16a, 16b is used, this benefit of withdrawing channel 20c first may or may not be needed.

Alternatively, if a cable/zip tie is used as means of tightening or closing 16a, 16b specimen-receiving opening 14, opening 14 can be sealed by pulling the cable/zip tie with grasper 28 or a knot pusher. Any known means of tightening or closing 16a, 16b is contemplated herein by the current invention.

At this point or at any suitable time, the camera (seen in FIGS. 3A-3B as reference numeral 31), which may be used to visualize the positioning/withdrawal of morcellator channel 20c (or other channel 20) and the placement of excised specimen 22 into interior 15 of retaining carrier 12, can be removed from a central (typically camera) port, if that is where the camera was inserted, and placed in a side port/trocar. Similar to FIG. 2A, grasper 28 can subsequently be inserted through respective camera port or skin incision 26 (under direct visualization of camera 31) and used to withdraw camera channel 20b of morcellation system 10 through laparoscopic port 26 formed for camera 31. Camera 31 can then be removed from the side trocar port and itself passed into interior 15 of retaining carrier 12 through camera channel 20b.

At this point or beforehand, grasper 28 can subsequently be inserted through laparoscopic port or skin incision 26 formed for control instruments and used to withdraw control instrument channel 20a of morcellation system 10 through respective control instrument port 26. Control instrument (such as grasper 28; see FIG. 3B) itself can then be passed into interior 23 of retaining carrier 12 through control instrument channel 20a.

An insufflation tube can then be attached to the camera trocar or optionally passed through a separate insufflation channel which would be inserted and withdrawn as discussed with the previous channels. The insufflation tube would insufflate the retaining carrier to distend. If needed, the channels can be sealed against the trocars with suture ties.

More specifically, if a separate port is used for insufflation channel 20d, grasper 28 can be inserted through laparoscopic port or skin incision 26 formed for an insufflation source and used to withdraw insufflation channel 20d of morcellation system 10 through respective insufflation port 26. Insufflation channel 20d itself can then be passed into interior 15 of retaining carrier 12 through insufflation channel 20d. The proximal end of insufflation channel 20d (i.e., the end closes to user 30) can be coupled to a conventional insufflation source (not shown) for pumping fluid (e.g., air) into carrier 12 through insufflation channel 20d for insufflating carrier 12. As such, because opening 14 has been tightened, cinched, or closed via means 16a, 16b, the fluid supplied by the insufflation source should be not be able to escape interior 15 of carrier 23, or at the very least, the fluid should be hindered from exiting interior 15 of carrier 23 if opening 14 has been tightened but not closed completely. Insufflating carrier 12 forms a protected environment in which user 30 can morcellate and remove targeted tissue 22 or otherwise perform the necessary procedures.

Figure 2A:
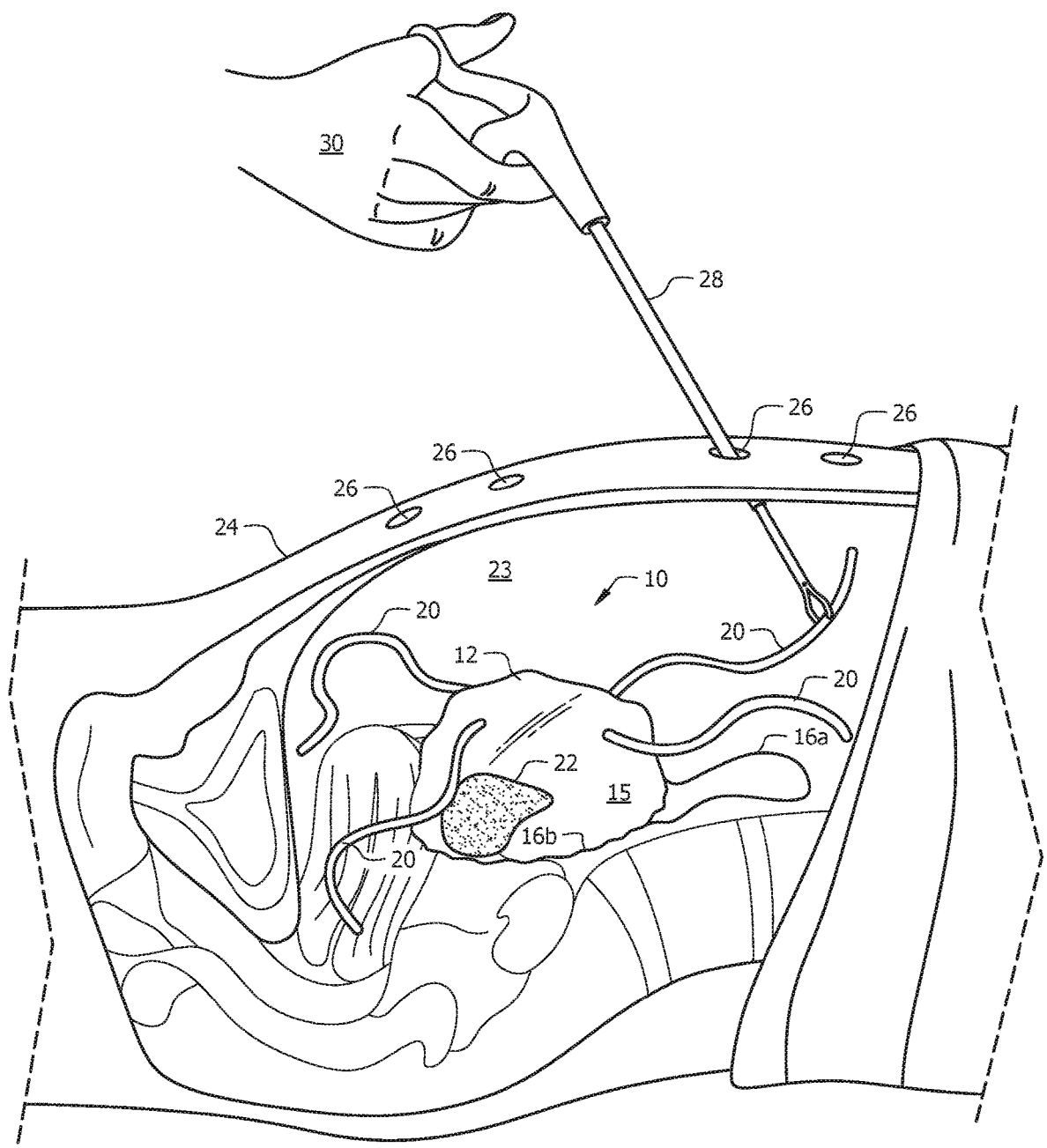
FIGS. 2A-2D depicts withdrawal of the channels from the cavity, along with depicting all four channels extending out of the cavity but without any laparoscopic tools inserted therein.
Figure 2B:
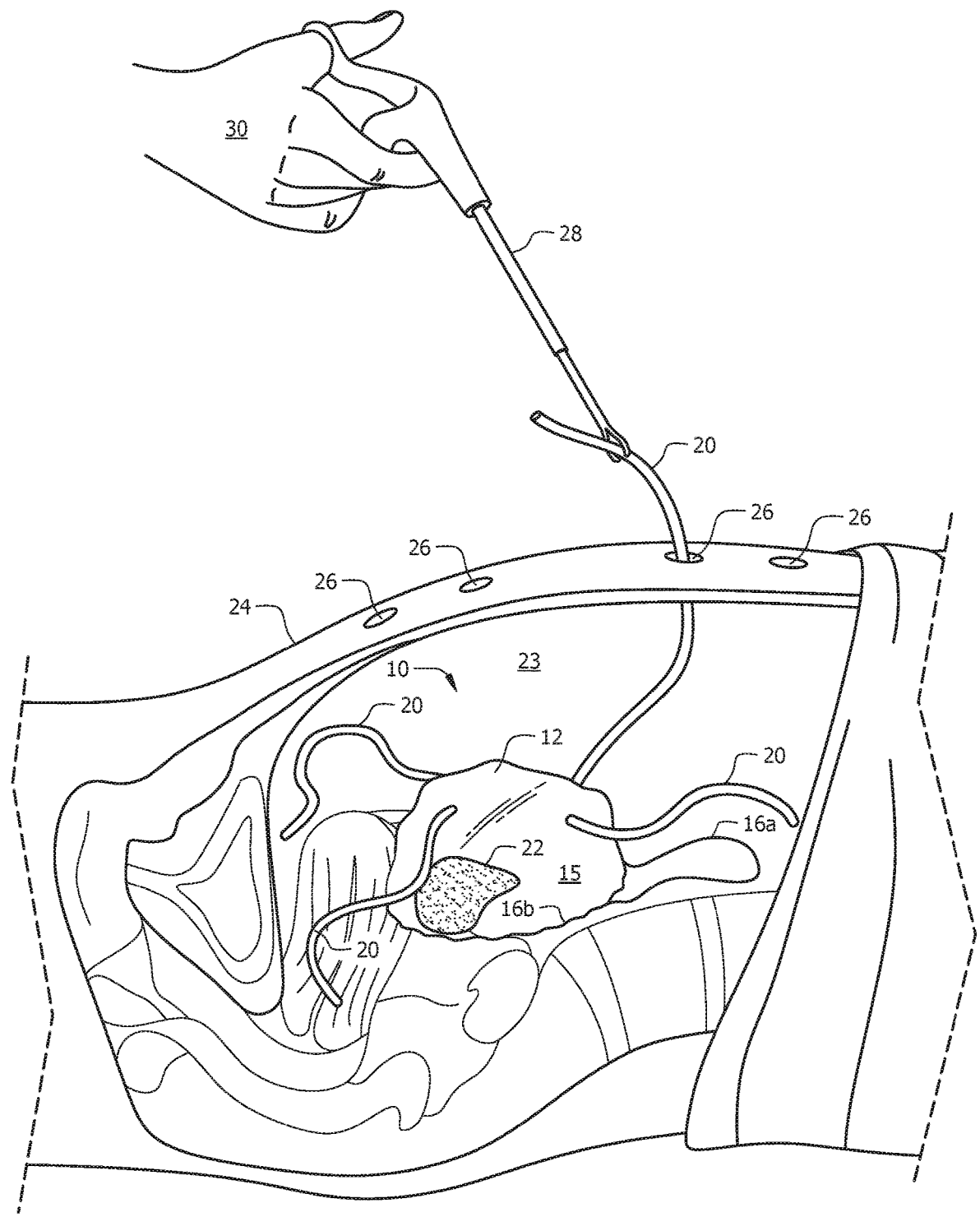
Figure 2C:
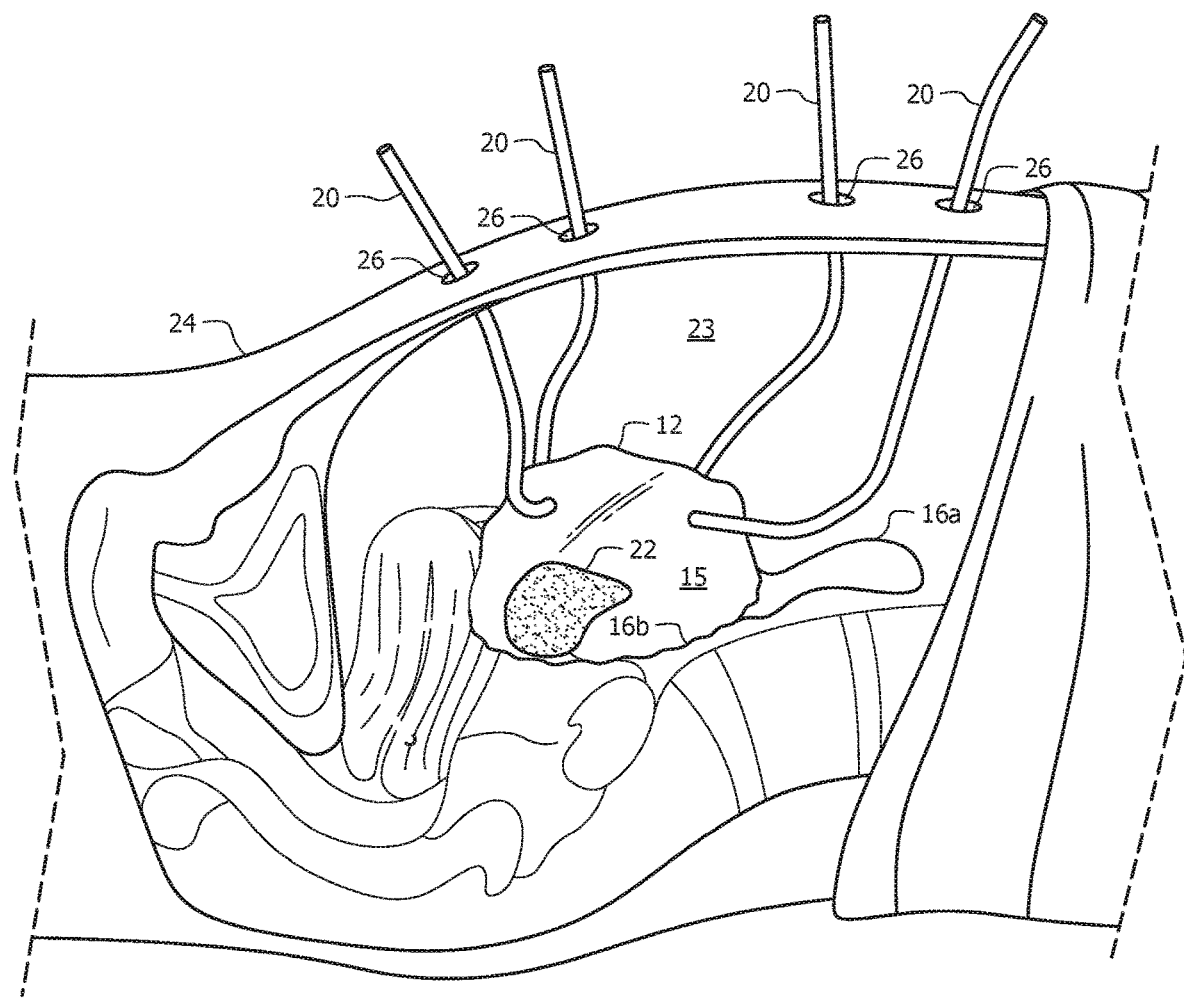
Figure 2D:
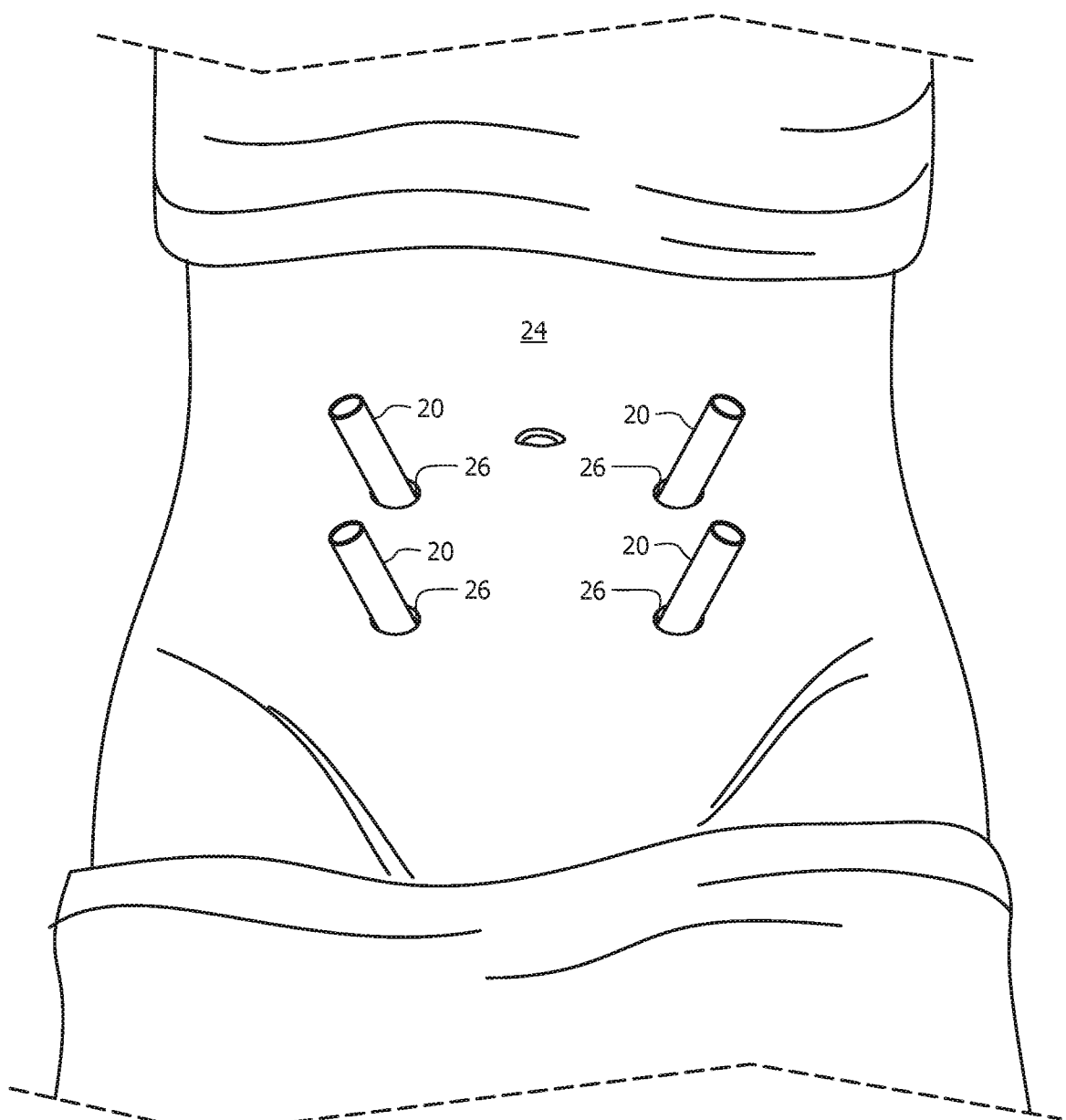

FIGS. 2A-2D generally depict a process of withdrawing channels 20 from operative cavity 23 of a subject or patient after insertion of system 10 into body 24 of the subject or patient. FIG. 2A shows a grasper inserted through laparoscopic port 26 into operative cavity 23 of the patient or subject, where grasper 28 has grasped one of channels 20 within cavity 23. FIG. 2B shows grasper 28 retracting and withdrawing channel 20 through port 26. FIGS. 2C-2D show channels 20 fully withdrawn through ports 26 after grasper 28 has released channels 20. It is contemplated herein, however, that FIGS. 2A-2D show just one way of withdrawing channels 20 through laparoscopic ports 26; channels 20 can be withdrawn through their respective ports 26 using any contemplated methodology. FIGS. 2C-2D show channels 20 withdrawn through the respective laparoscopic ports 26 without any laparoscopic tools or trocars inserted into channels 20.

Regardless of the order of the foregoing steps of withdrawing channels 20 from operative cavity 23 and actuating means 16a, 16b to tighten or close opening 20, the ultimate goal is for channels 20 to be withdrawn from cavity 23 and for targeted specimen to be substantially sealed within interior 15 of carrier 12. As can be understood, this goal can be accomplished in a variety of manners, regardless of which of channels 20 are withdrawn first, when opening 20 is closed, etc.

Referring back to the exemplary methodology, at this point, channels 20a-20d have been pulled and withdrawn through laparoscopic ports 26, respectively, such that the free proximal end of each of channels 20a-20d are external to body 24 of the subject, and excised specimen 22 is sealed within interior 15 of carrier 12 after actuation of means 16a, 16b. As seen in FIG. 3B, control instrument 28, camera 31, morcellator 32, and insufflation source 34 extend into or are in communication with substantially hollow interior 15 of carrier 12. As discussed, for each channel 20a-20d that is withdrawn from body 24 of the subject through its respective port 26, a suture tag (not shown) can be attached to the free proximal end of each channel 20a-20d in order facilitate the withdrawal of channels 20a-20d from operative cavity 23 of the subject.

Figure 4:
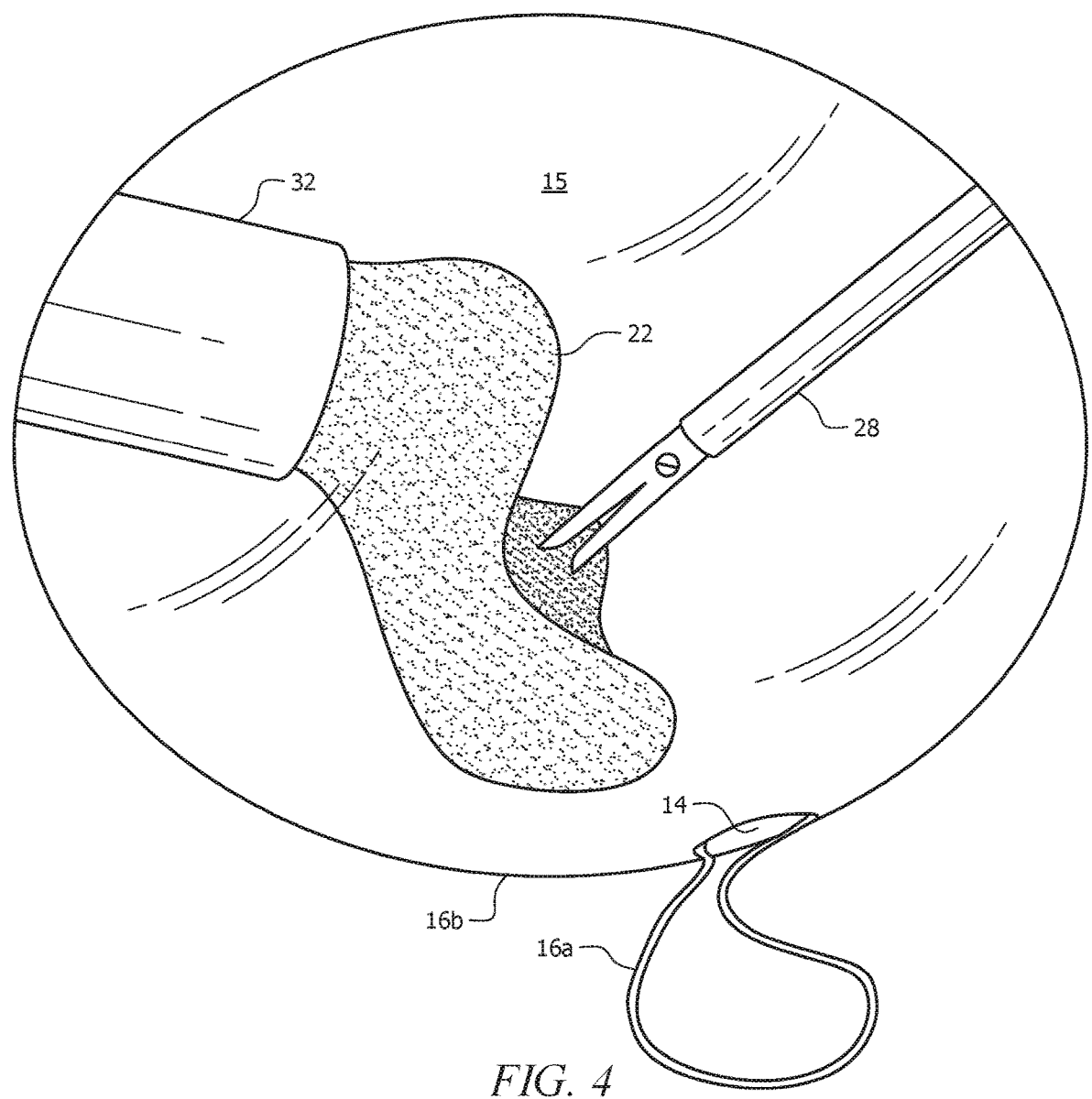
FIG. 4 is a view within an insufflated retaining bag through a laparoscopic camera, showing the control instrument and morcellator during morcellation of the blue specimen.

With these components of morcellation system 10 in place, morcellation of excised specimen/tissue 22 is performed under direct visualization of camera 31 (inserted through camera channel 20b), where fragments of specimen 22 can be morcellated and withdrawn by morcellator 32 through morcellator channel 20c and respective port 26. FIG. 4 shows a view from camera 31 within insufflated carrier 12, where control instrument 28 holds specimen 22 and morcellator 32 morcellates and removes specimen 22.

Figure 5A:
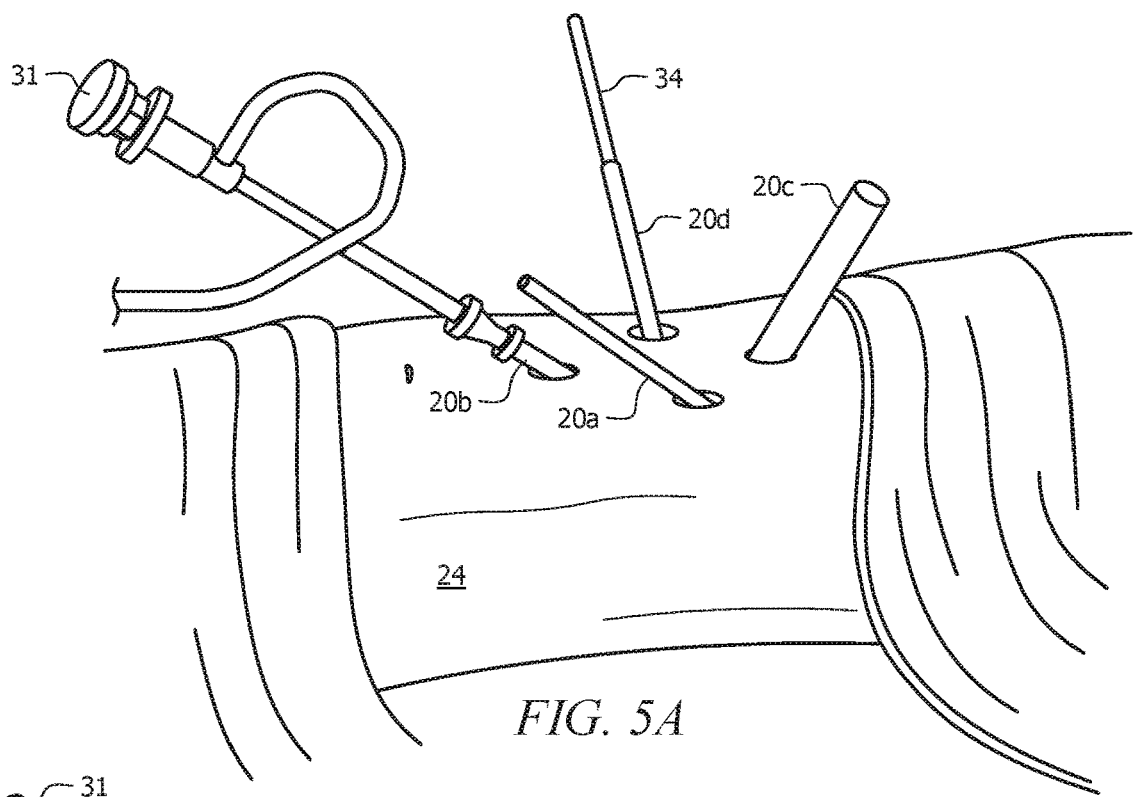
FIGS. 5A-5D depict a process of removal of the morcellation system from the subject's body.

After morcellation is satisfactorily completed, retaining carrier 12 can be completely desufflated. Control instrument 28 and morcellator 32 can be withdrawn from channels 20a and 20c, respectively, with their respective trocars, leaving control instrument channel 20a and morcellation channel 20c extending externally from body 24 of the subject (FIG. 5A). The free/proximal end of control instrument channel 20c can be tied off, and channel 20c itself can be pushed back into operative cavity 23 of the subject. Removal of insufflation source 34 and insufflation port 20d can occur in substantially a similar manner. See FIG. 5B.

Figure 5B:
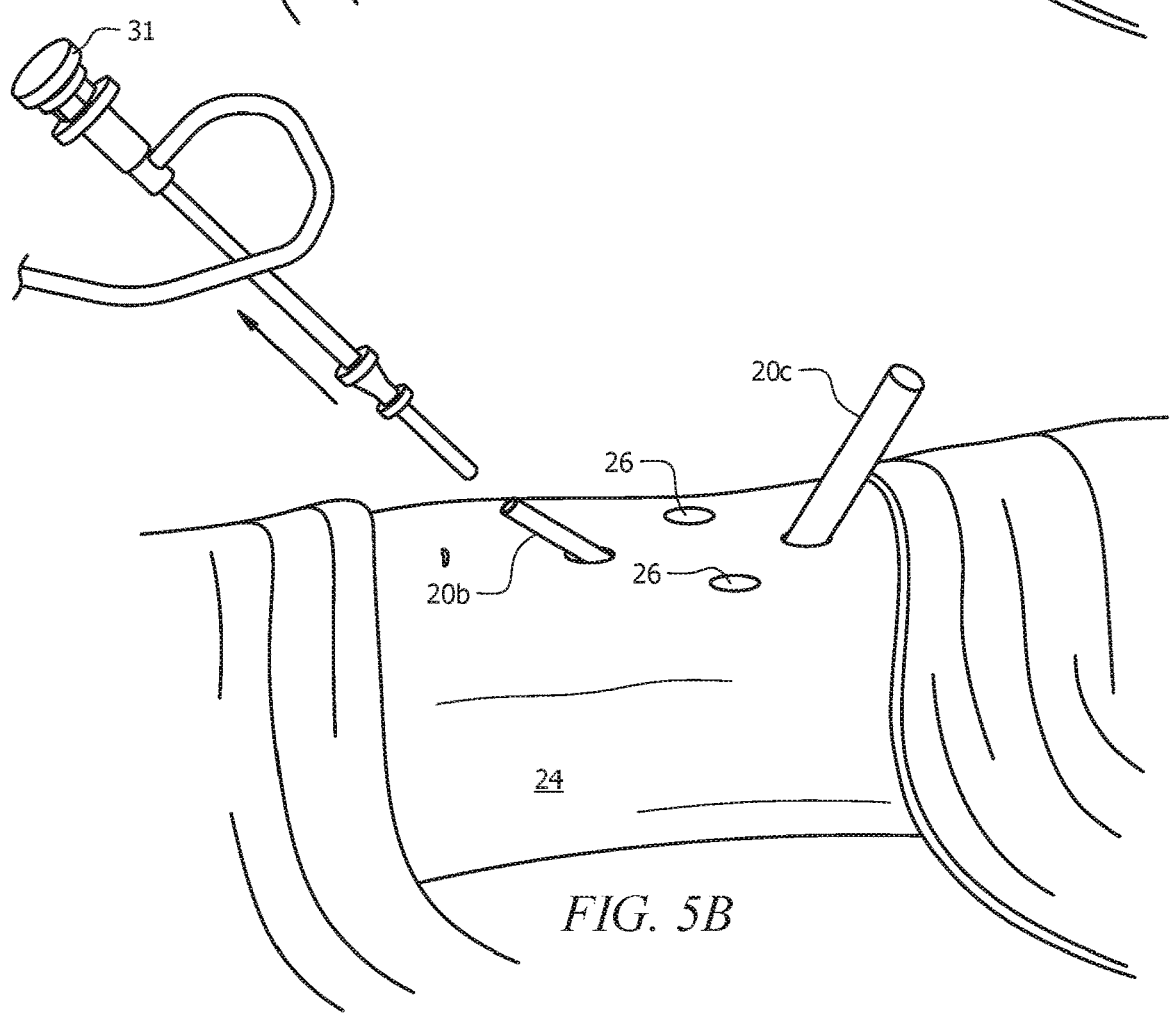
Figure 5C:
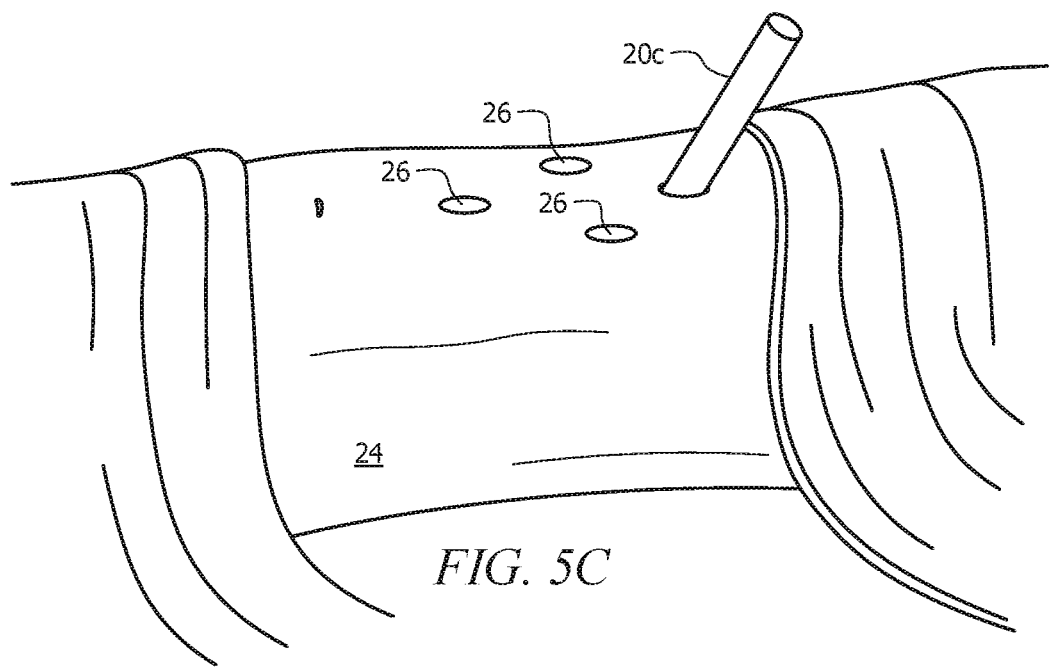

Camera 31 may remain in camera channel 20b through this process for the purpose of visualization, but beforehand or afterwards, camera 31 can be withdrawn from camera channel 20b with its respective trocar, leaving camera channel 20b extending externally from body 24 of the subject (FIG. 5B). The free/proximal end of camera channel 20b can be tied off, and channel 20b itself can be pushed back into operative cavity 23 of the subject. See FIG. 5C.

Figure 5D:
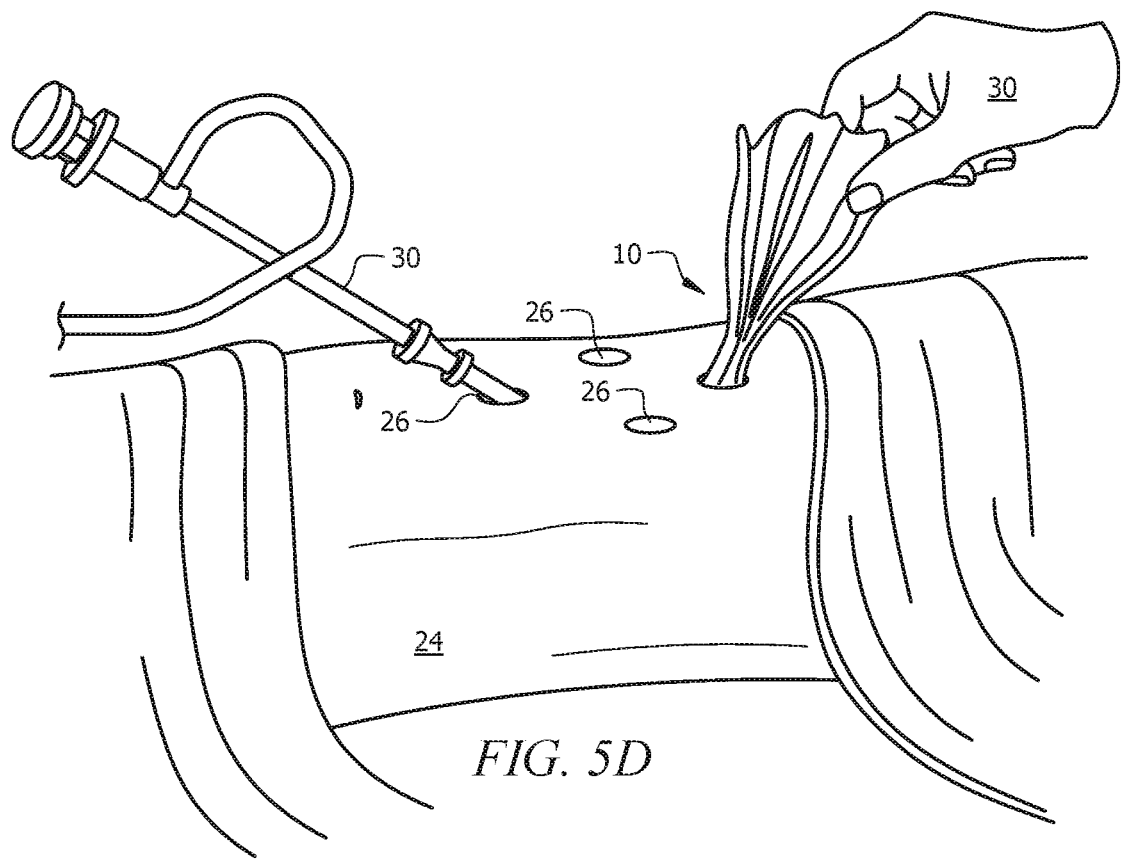

Morcellator 32 can be removed, if not previously removed, and subsequently, the intact, desufflated retaining carrier 12, along with control instrument channel 20a, camera channel 20b, and camera channel 20c—all of which are within body 24 of the subject—can be withdrawn via laparoscopic port 26 that was formed for morcellator 32 (assuming the morcellator port is the largest in size). To do this, as can be seen in FIG. 5D, user 30 can simply pull morcellator channel 20c to withdraw pliable carrier 12 and pliable channels 20a-20d from interior 23 of body 24 of the subject. Though typically morcellator channel 20c is largest in size/diameter, it is contemplated herein that removal of system 10 can occur through any suitable port 26.

Regardless of the order of the foregoing steps of removing the laparoscopic tools from channels 20 or how cavity 23 is visualized or which of channels 20 are inserted back into cavity 23, the ultimate goal is for system 10 to be entirely withdrawn from cavity 23 through at least one of laparoscopic ports 24. As can be understood, this goal can be accomplished in a variety of manners, regardless of which of tools are removed first, which of channels 20 are pushed into cavity 23, which of ports 24 is used for withdrawing system 10, etc.

Figure 6:
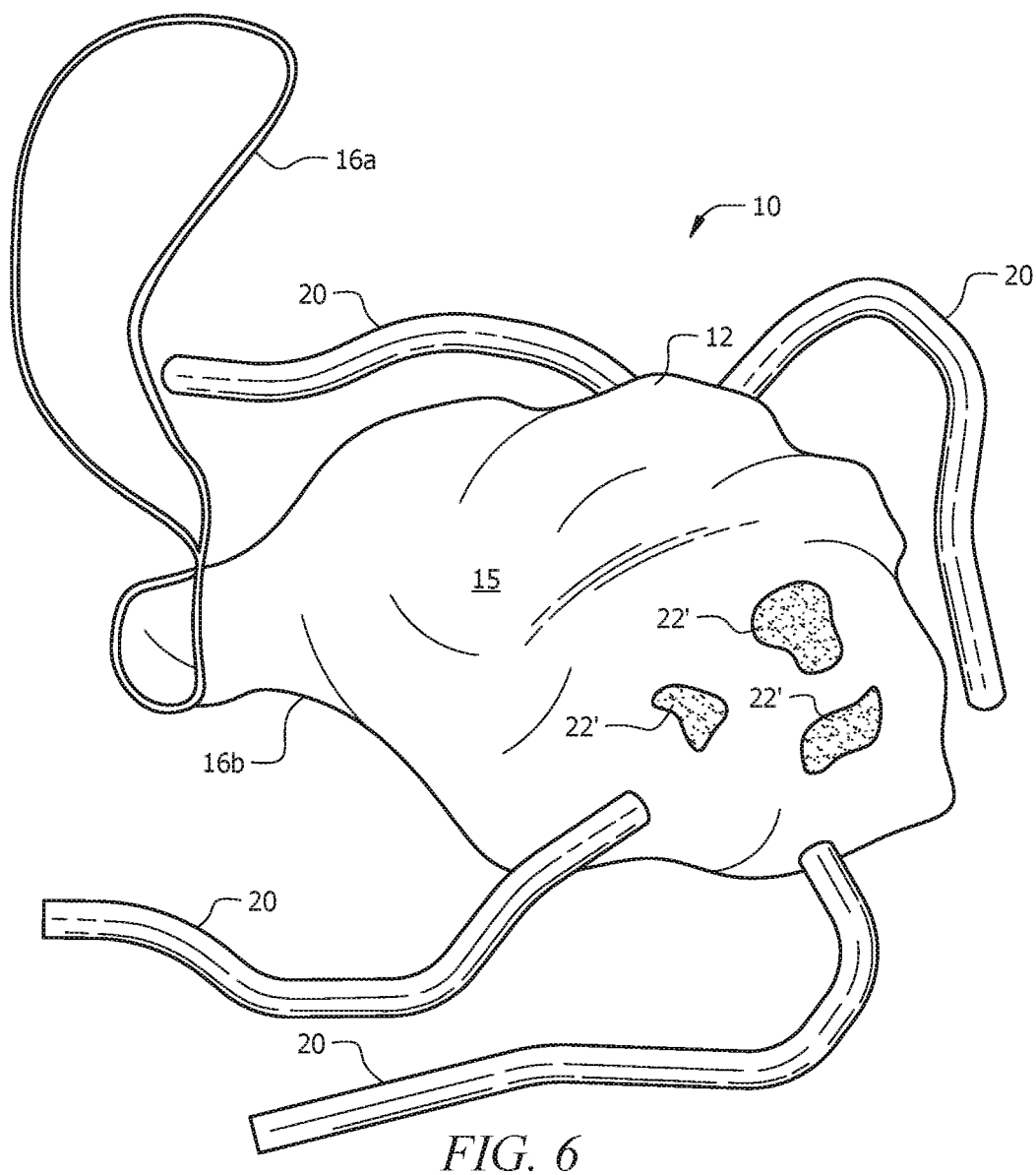
FIG. 6 depicts remnants of the specimen remaining contained within the retaining bag even after morcellation and removal of the retaining bag from the abdominal/pelvic cavity of the subject or patient.

As can be seen in FIG. 6, remnants 22' of specimen 22 that were not withdrawn via morcellator 32 remain contained within retaining carrier 12 throughout the morcellation procedure and even after withdrawal from body 24 of the subject.

At this point, all laparoscopic instruments can be cleaned and replaced in the laparoscopic ports, as necessary, to inspect operative/peritoneal cavity 23. When satisfied, the port fascia can be closed using known methods. The remaining procedure can be performed using known methods as well.

Glossary of Claim Terms

Applying a force: This term is used herein to refer to an act of manipulating a structure to act in a manner desired. As an example of the current invention, a pulling force can be applied to a withdrawn channel in order to extract the entire morcellation system (and components thereof, i.e., retaining carrier, other channels, etc.) from the inside of a patient or subject.

Control instrument: This term is used herein to refer to any laparoscopic tool that can be used in holding or stabilizing a specimen or tissue during operation of the surgical procedure, for example during morcellation of the specimen or tissue.

Desufflate: This term is used herein to refer to a fluid (e.g., gas) exiting a wholly or partially inflated reservoir or carrier such that the reservoir or carrier is no longer inflated.

Direct visualization: This term is used herein to refer to the ability of a user or operator (e.g., surgeon) to consistently see or recognize the procedure being performed within the interior of the subject or patient.

Distal: This term is used herein to refer to a position of a structure that is closer to the interior of a subject or patient than another structure that is closer to a user or operator (e.g., surgeon).

Drawstring-type apparatus: This term is used herein to refer to a string, cord, or similar structure lining the perimeter of an opening and laced through eyelets for use in tightening, cinching, closing, or sealing off the opening.

Insufflate: This term is used herein to refer to pumping a fluid (e.g., gas) into the interior of a reservoir or carrier in order to inflate the reservoir or carrier, thus providing a substantially open space for conducting the medical procedure at hand.

Laparoscopic port: This term is used herein to refer to an incision or aperture in the skin or body of a subject or patient that leads from an environment external to the body of the subject to an environment internal to the body of the subject. It is contemplated herein that a laparoscopic port can, for example, be an incision leading to the peritoneal cavity of the subject or even be a vagina of a female subject.

Laparoscopic tool: This term is used herein to refer to a surgical instrument that can be used during minimally invasive surgery, where the laparoscopic tool can be inserted through a laparoscopic port.

Lining: This term is used herein to refer to a layer of material that lines the interior or exterior of a bag, pouch, or carrier.

Means of tightening, cinching, closing, or sealing: This term is used herein to refer to any suitable apparatus or methodology of enclosing a targeted specimen/tissue within a carrier, such that the interior of the carrier is not in completely open communication with an environment external to the carrier.

Operative internal cavity: This term is used herein to refer to space within a subject or patient where a medical procedure is intended to take place. Examples of operative internal cavities include, but are not limited to, peritoneal cavities, abdominal cavities, and pelvic cavities.

Proximal: This term is used herein to refer to a position of a structure that is closer to a user or operator (e.g., surgeon) than another structure that is closer to the interior of a subject or patient.

Retaining carrier: This term is used herein to refer to a resilient bag or pouch that has an opening for receiving a specimen/tissue, where the bag or pouch can enclose the specimen/tissue and create an environment for performing a medical procedure on the specimen/tissue.

Suture tag: This term is used herein to refer to an apparatus connected to a channel according to the current invention and use for the purpose of facilitating manipulation of the channel (e.g., withdrawing the channel through the laparoscopic port).

Targeted specimen: This term is used herein to refer to tissue within a subject or patient intended to undergo a medical procedure, for example morcellation and removal from the subject or patient.

Withdraw: This term is used herein to refer to extracting an object or component from the interior of a body of a subject or patient and pulling/bringing it to the exterior of the body of the subject or patient (e.g., through a laparoscopic port). The object or component can be withdrawn partially or fully. For example, a channel can be withdrawn such that a portion (typically a majority) of the channel is positioned outside of the body and a portion of the channel is still positioned inside of the body. As another example, a morcellation system can be withdrawn from the interior of the body by extracting the entire apparatus from the interior of the body, such that no remaining portion of the system remains inside the body.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A morcellation system, comprising:
    a pliable retaining carrier or pouch with a specimen-receiving opening that leads from an exterior of said retaining carrier to a substantially hollow interior of said retaining carrier,
    said retaining carrier insertable into an operative internal cavity of a subject or patient,
    said retaining carrier structured to receive a targeted, excised specimen within said substantially hollow interior; and
    a plurality of elongate, flexible laparoscopic tool- or trocar-receiving channels extending externally from a lining of said retaining carrier at a spaced distance away from said specimen-receiving opening and at a spaced distance away from each other,
    said plurality of channels each having a proximal end and a distal end, said proximal end configured to be withdrawn external to said body of said subject when said morcellation system has been inserted into said patient or subject,
    said retaining carrier having a first position and a second position, said first position being a desufflated position within said operative internal cavity of said subject with said specimen-receiving opening being open, said second position being an insufflated position within said operative internal cavity of said subject with said specimen-receiving opening being closed or cinched, wherein said each channel is extended through a respective laparoscopic port on said body.

2. The morcellation system of claim 1, further comprising:
said operative internal cavity of said subject or patient being an abdominal or pelvic cavity.

3. The morcellation system of claim 1, further comprising:
said plurality of channels structured to receive one or more laparoscopic tools,
said one or more laparoscopic tools selected from the group consisting of a trocar, a morcellator, a camera, a control instrument, and an insufflation source.

4. The morcellation system of claim 1, further comprising:
a means of tightening, cinching, closing, or sealing said specimen-receiving opening positioned on a perimeter of said specimen-receiving opening,
said means of tightening, cinching, closing, or sealing said specimen-receiving opening being a drawstring-type apparatus that is pulled relative to said specimen-receiving opening in order to reduce a diameter or length of said specimen-receiving opening.

5. The morcellation system of claim 1, further comprising:
said plurality of channels including a morcellator channel structured to receive a morcellator, a control instrument channel structured to receive a control instrument, and a camera channel structured to receive a camera, so that said morcellator can morcellate said targeted specimen within said substantially hollow interior of said retaining carrier under direct visualization of said camera while said control instrument holds said targeted specimen.

6. The morcellation system of claim 1, further comprising:
an elongate suture tag attached to and positioned at said proximal end of said each channel to facilitate laparoscopic manipulation of said each channel.

7. The morcellation system of claim 1, further comprising:
said second position of said retaining carrier further including said closed or cinched specimen-receiving opening configured to be pressed against an anterior abdominal wall within said subject when said operative internal cavity is an abdominal or pelvic cavity of said subject.

8. The morcellation system of claim 1, further comprising:
said plurality of channels positioned on said lining of said retaining carrier such that said plurality of channels are configured to line up with laparoscopic ports on a body of said subject,
said distal end of said each channel terminating at said lining of said retaining carrier within said operative internal cavity of said subject.

9. A method of performing minimally invasive laparoscopic surgery on a subject, comprising:
providing a plurality of laparoscopic ports in a body of said subject;
excising a targeted specimen within an operative internal cavity of said subject;
inserting a morcellation system in a deflated position into said operative internal cavity of said subject, said morcellation system including a pliable retaining carrier having a substantially hollow interior and a closable or sealable specimen-receiving opening, said specimen-receiving opening providing for completely open communication between said operative internal cavity of said subject and said substantially hollow interior of said retaining carrier,
said morcellation system further including a plurality of laparoscopic tool- or trocar-receiving channels extending from a lining of said retaining carrier, said plurality of channels having an interior being in open communication with said substantially hollow interior of said retaining carrier, said plurality of channels positioned at a spaced distance away from said specimen-receiving opening and at a spaced distance away from each other;
withdrawing each of said plurality of channels from said operative internal cavity through a respective spatially aligned laparoscopic port of said plurality of laparoscopic ports;
positioning said excised, targeted specimen within said substantially hollow interior of said retaining carrier through said specimen-receiving opening;
inserting one or more laparoscopic tools into at least one of said plurality of channels, wherein said laparoscopic tool has a distal end disposed within said substantially hollow interior of said retaining carrier and a proximal end disposed external to said body of said subject;
insufflating said retaining carrier to distend in order to form a protected environment;
morcellating said excised, targeted specimen within said insufflated retaining carrier in order to remove at least a majority of said excised, targeted specimen from said operative internal cavity of said subject;
desufflating said retaining carrier; and
withdrawing said morcellation system including said retaining carrier and said plurality of channels from said operative internal cavity through a laparoscopic port of said plurality of laparoscopic ports, said retaining carrier enclosing any remnants of said excised, targeted specimen in said substantially hollow interior.

10. The method of claim 9, further comprising:
said operative internal cavity of said subject or patient being an abdominal or pelvic cavity.

11. The method of claim 9, further comprising:
said one or more laparoscopic tools selected from the group consisting of a trocar, a morcellator, a camera, a control instrument, and an insufflation source.

12. The method of claim 9, further comprising:
said step of tightening, cinching, closing, or sealing said specimen-receiving opening performed using a drawstring-type apparatus that is pulled relative to said specimen-receiving opening in order to reduce a diameter or length of said specimen-receiving opening.

13. The method of claim 9, further comprising:
said plurality of channels including a morcellator channel structured to receive a morcellator, a control instrument channel structured to receive a control instrument, and a camera channel structured to receive a camera, so that said morcellator can morcellate said targeted specimen within said protected environment of said morcellation system.

14. The method of claim 9, further comprising:
said each channel including an elongate suture tag attached to and positioned at said second end of said each channel to facilitate laparoscopic manipulation of said each channel.

15. The method of claim 9, further comprising:
said excised, targeted specimen being a uterus in a female subject.

16. The method of claim 9, further comprising the step of:
tightening said specimen-receiving opening to enclose said excised, targeted specimen within said substantially hollow interior of said retaining carrier, such that said substantially hollow interior of said retaining carrier is not in completely open communication with said operative internal cavity of said subject; and positioning said tightened, cinched, closed, or sealed specimen-receiving opening against an anterior abdominal or pelvic wall within said subject when said operative internal cavity is an abdominal or pelvic cavity of said subject.

17. The method of claim 9, further comprising:

said step of withdrawing said each channel from said operative internal cavity performed by:
- inserting a grasper into a first laparoscopic port of said plurality of laparoscopic ports and withdrawing a first channel of said plurality of channels through said first laparoscopic port, and
- inserting said grasper into a second laparoscopic port of said plurality of laparoscopic ports and withdrawing a second channel of said plurality of channels through said second laparoscopic port, wherein said step of tightening, cinching, closing, or sealing said specimen-receiving opening is performed after withdrawing said first channel but before withdrawing said second channel.

18. The method of claim 9, further comprising:

said step of withdrawing said morcellation system from said operative internal cavity performed by:
- inserting said each channel into said operative internal cavity except for one (1) of said plurality of channels, and
- applying a force to said one channel in order to extract said retaining carrier and said each channel from said operative internal cavity.

19. The method of claim 9, further comprising:

performing each of the steps of said method of performing minimally invasive laparoscopic surgery on said subject under direct visualization of a camera.

20. A method of performing a hysterectomy on a subject, comprising:

providing a plurality of laparoscopic ports in a body of said subject;

excising a targeted specimen within an operative internal cavity of said subject, said operative internal cavity of said subject or patient being an abdominal or pelvic cavity, said excised, targeted specimen being a uterus in a female subject;

inserting a morcellation system in a deflated position into said operative internal cavity of said subject, said morcellation system including a pliable retaining carrier having a substantially hollow interior and a closable or sealable specimen-receiving opening, said specimen-receiving opening providing for completely open communication between said operative internal cavity of said subject and said substantially hollow interior of said retaining carrier, said morcellation system further including a plurality of laparoscopic tool- or trocar-receiving channels extending from a lining of said retaining carrier, said plurality of channels having an interior being in open communication with said substantially hollow interior of said retaining carrier, said plurality of channels positioned at a spaced distance away from said specimen-receiving opening and at a spaced distance away from each other, said plurality of channels being spatially aligned with said plurality of laparoscopic ports, said each channel having a first end that terminates at said lining of said retaining carrier within said operative internal cavity of said subject and a second end that is external to said body of said subject, inserting a grasper into a first laparoscopic port of said plurality of laparoscopic ports and withdrawing a first channel of said plurality of channels through said first laparoscopic port;

positioning said excised, targeted specimen within said substantially hollow interior of said retaining carrier through said specimen-receiving opening;

tightening said specimen-receiving opening to enclose said excised, targeted specimen within said substantially hollow interior of said retaining carrier, such that said substantially hollow interior of said retaining carrier is not in completely open communication with said operative internal cavity of said subject, wherein said step of tightening, cinching, closing, or sealing said specimen-receiving opening is performed using a drawstring-type apparatus that is pulled relative to said specimen-receiving opening in order to reduce a diameter or length of said specimen-receiving opening;

inserting said grasper into a second laparoscopic port of said plurality of laparoscopic ports and withdrawing a second channel of said plurality of channels through said second laparoscopic port, such that said each channel is withdrawn from said operative internal cavity through a respective spatially aligned laparoscopic port of said plurality of laparoscopic ports;

inserting one or more laparoscopic tools into at least one of said plurality of channels, wherein each of said one or more laparoscopic tools has a distal end disposed within said substantially hollow interior of said retaining carrier and a proximal end disposed external to said body of said subject, wherein at least one of said one or more laparoscopic tools is selected from the group consisting of a trocar, a morcellator, a camera, a control instrument, and an insufflation source;

positioning said tightened, cinched, closed, or sealed specimen-receiving opening against an anterior abdominal or pelvic wall within said subject;

insufflating said retaining carrier to distend in order to form a protected environment;

morcellating said excised, targeted specimen within said insufflated retaining carrier in order to remove at least a majority of said excised, targeted specimen from said operative internal cavity of said subject;

desufflating said retaining carrier;

withdrawing said morcellation system including said retaining carrier and said plurality of channels from said operative internal cavity through a laparoscopic port of said plurality of laparoscopic ports, said retaining carrier enclosing any remnants of said excised, targeted specimen in said substantially hollow interior; and performing each of the foregoing steps of said method of performing minimally invasive laparoscopic surgery on said subject under direct visualization of a camera.

* * * * *